（12) United States Patent
Frey et al.

(10) Patent No.: US 10,653,445 B2
(45) Date of Patent: May 19, 2020

(54) SENSOR INSERTION ASSEMBLY, SENSOR CARTRIDGE, AND INSERTER

(71) Applicant: Roche Diagnostics Operations, Inc., Indianapolis, IN (US)

(72) Inventors: Stephan-Michael Frey, Griesheim (DE); Oliver Kube, Worms (DE); Helmut Walter, Heppenheim (DE); Wolfgang Heck, Frankenthal (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1035 days.

(21) Appl. No.: 14/553,380

(22) Filed: Nov. 25, 2014

(65) Prior Publication Data
US 2015/0080684 A1 Mar. 19, 2015

Related U.S. Application Data

(63) Continuation of application No. PCT/EP2013/060367, filed on May 21, 2013.

(30) Foreign Application Priority Data

May 31, 2012 (EP) ..................................... 12170223

(51) Int. Cl.
*A61B 17/34* (2006.01)
*A61B 5/145* (2006.01)
(Continued)

(52) U.S. Cl.
CPC ...... *A61B 17/3468* (2013.01); *A61B 5/14503* (2013.01); *A61B 5/14532* (2013.01);
(Continued)

(58) Field of Classification Search
CPC ............ A61B 17/3468; A61B 5/14546; A61B 5/14503; A61B 5/14542; A61B 5/6849;
(Continued)

(56) References Cited

U.S. PATENT DOCUMENTS 5,074,318 A * 12/1991 Campbell ............ A01K 11/006
128/899
5,267,972 A * 12/1993 Anderson ........... A61M 5/3271
604/192
(Continued)

FOREIGN PATENT DOCUMENTS

WO WO 00/69492 A1 11/2000
WO WO 2008/065646 A1 6/2008

OTHER PUBLICATIONS

International Search Report and Written Opinion of the International Searching Authority, PCT/EP2013/060367, dated Sep. 30, 2013.

*Primary Examiner* — Erich G Herbermann
(74) *Attorney, Agent, or Firm* — Bose McKinney & Evans LLP

(57) ABSTRACT

A sensor insertion assembly comprising a sensor cartridge having an insertion needle and a sensor within a sterile capsule. The sensor insertion assembly further comprises an inserter comprising a chamber for receiving the sensor cartridge, wherein the inserter further comprises an insertion mechanism operable for actuating the insertion needle for inserting the sensor into a subject. The sensor cartridge is removable from the chamber. The sensor cartridge is operable for shielding the insertion needle upon removal of the sensor cartridge from the chamber.

26 Claims, 9 Drawing Sheets

(51) Int. Cl.
*A61B 5/00* (2006.01)
*A61B 5/1486* (2006.01)
*A61B 17/00* (2006.01)

(52) U.S. Cl.
CPC ...... *A61B 5/14542* (2013.01); *A61B 5/14546* (2013.01); *A61B 5/14865* (2013.01); *A61B 5/6849* (2013.01); *A61B 2017/00469* (2013.01); *A61B 2560/063* (2013.01)

(58) Field of Classification Search
CPC .......... A61B 5/14532; A61B 5/150312; A61B 5/15176; A61B 5/15178; A61B 5/15184
See application file for complete search history.

(56) References Cited

U.S. PATENT DOCUMENTS

| | | | |
|---|---|---|---|
| 5,390,671 A | 2/1995 | Lord et al. | |
| 5,868,711 A * | 2/1999 | Kramer | A61B 17/3472 604/136 |
| 6,468,264 B1 * | 10/2002 | Gillis | A61M 37/00 604/513 |
| 7,927,345 B2 * | 4/2011 | Berkovitch | A61B 5/15146 606/181 |
| 7,946,984 B2 * | 5/2011 | Brister | A61B 5/0002 600/347 |
| 8,002,752 B2 | 8/2011 | Yodfat et al. | |
| 2004/0260270 A1 * | 12/2004 | Cohen | A61M 5/20 604/506 |
| 2006/0020189 A1 * | 1/2006 | Brister | A61B 5/0002 600/345 |
| 2008/0125801 A1 * | 5/2008 | List | A61B 5/150022 606/181 |
| 2008/0242962 A1 | 10/2008 | Roesicke et al. | |
| 2008/0255440 A1 | 10/2008 | Eilersen et al. | |
| 2008/0319414 A1 | 12/2008 | Yodfat et al. | |
| 2008/0319416 A1 * | 12/2008 | Yodfat | A61B 5/6849 604/513 |
| 2013/0060105 A1 * | 3/2013 | Shah | A61B 5/6849 600/316 |

\* cited by examiner

SENSOR INSERTION ASSEMBLY, SENSOR CARTRIDGE, AND INSERTER

RELATED APPLICATIONS

This application is a continuation of PCT/EP2013/060367, filed May 21, 2013, which claims priority to EP 12170223.7, filed May 31, 2012, both of which are hereby incorporated herein by reference in their entireties.

BACKGROUND

The invention relates to sensors for in vivo monitoring of an analyte, in particular to devices for inserting a sensor into a subject.

For the proper management of chronic health conditions it may be crucial for a subject to periodically monitor one or more analyte levels in his or her blood stream. In the case of diabetes the subject routinely monitors the glucose levels to avoid hypoglycemic episodes and hyperglycemic episodes. For other situations where health monitoring is important, other analytes, such as lactate or oxygen, may be measured.

A typical means of performing such monitoring is the repeated drawing of blood by the subject to provide a sample for analysis by a monitoring system. This provides a cost effective way monitoring chronic diseases such as diabetes, but it may be inconvenient and only provides data on the analyte concentration at the time intervals when the test was performed.

Systems have also been developed which allow a sensor to be implanted into a subject to monitor the analyte concentration directly within the bloodstream or within the interstitial fluids. For instance, an electrochemical sensor may be inserted into a subcutaneous region of the subject where the analyte concentration is continuously monitored and/or logged.

For instance, United States patent application US 2008/0242962 A1 discloses a monitoring system for monitoring analyte concentration, such as glucose, with an implantable sensor.

A disadvantage of current systems for inserting subcutaneous sensor systems is that the they may require that an inserter is used each time a sensor is inserted into a subject. This may require the disposal of the inserter.

SUMMARY

This disclosure teaches a sensor insertion assembly, a sensor cartridge, and an inserter. In one aspect, a sensor insertion assembly is disclosed comprising a sensor cartridge comprising an insertion needle and a sensor within a sterile capsule. The insertion needle may be a hollow needle with a cross-section that has been removed. For example, the needle may have a cross-section that resembles the letter "c." This enables the insertion needle to insert the sensor and then remove the needle while leaving the sensor within a subject. The sterile capsule keeps the insertion needle and the sensor sterile in order to prevent an infection in a subject. The sensor insertion assembly further comprises an inserter comprising a chamber for receiving the sensor cartridge.

The inserter further comprises an insertion mechanism, or actuator, operable for actuating the insertion needle for inserting the sensor into a subject. The sensor cartridge is removable from the chamber. The sensor cartridge is operable for shielding the insertion needle upon removal of the sensor cartridge from the chamber. This embodiment may have several advantages. Being able to insert a sensor cartridge into the inserter and remove it after use may be advantageous because the inserter may be reused. This reduces waste produced by the use of the inserter and may also reduce the costs. The use of a sensor cartridge may be advantageous because the insertion needle is protected after use. This may eliminate the need for a patient, particularly a home patient, to have his or her own sharps container.

In another embodiment, the insertion mechanism is operable for removing at least a portion of the insertion needle from the sterile capsule a predetermined time before inserting the sensor into the subject. The embodiment may be beneficial because the insertion needle is kept sterile for as long as possible before insertion into the subject. From the point of view of a subject or operator of the sensor insertion assembly the removal of the insertion needle from the sterile capsule and inserting the sensor into the subject occur simultaneously. The subject or operator performs one action and the insertion needle at least partially leaves the sterile capsule and then the insertion needle inserts the sensor into the subject.

In another embodiment, the sensor insertion assembly further comprises a failsafe mechanism which is operable for permitting the actuation of the insertion needle only once. This may be advantageous because it prevents the same insertion needle from being used twice. This reduces the chance of injury due to the insertion needle and may also reduce the chance of spreading infection when a needle is used by more than one subject. In one embodiment, the sensor insertion assembly may be operable for resetting the fail safe mechanism when the sensor cartridge is inserted into the chamber. This may be advantageous because the fail safe ensures that the needle is used only once and when the sensor cartridge is inserted into the chamber ensures that the fail safe mechanism is in the proper state. Alternatively, the sensor assembly may be operable for resetting the fail safe mechanism when a sensor cartridge is removed from the chamber. This embodiment may have the advantage that the sensor insertion assembly does not need to be reset when a new cartridge is inserted into the chamber.

In one embodiment, the fail safe is incorporated into the sensor cartridge. In embodiments where there are multiple sensor cartridges, the fail safe may be incorporated into each of the multiple sensor cartridges. This embodiment may be beneficial because it prevents a particular sensor cartridge from being used more than once.

In another embodiment, the sensor insertion assembly comprises a magazine comprising multiple sensor cartridges. The inserter is operable for reloading a second sensor cartridge into the chamber from the magazine after actuation of the insertion mechanism. This embodiment may be advantageous because it may simplify the use of the sensor insertion assembly. For instance a healthcare provider could provide a patient with a sensor insertion assembly that has been loaded with a cartridge. When the subject visits the doctor's office or is visited by a nurse at home the healthcare provider could change the magazine for the patient.

In another embodiment, the magazine is a linear magazine. For instance the linear magazine could contain multiple sensor cartridges aligned in a linear fashion.

In another embodiment, the magazine is a cylindrical magazine. In this embodiment the magazines may be arranged in a cylindrical fashion. The sensor insertion assembly could therefore have a revolver-like arrangement for loading and unloading the sensor cartridges.

In another embodiment, the magazine is operable for shielding of the insertion needle after actuation of the insertion mechanism. For instance after use the sensor cartridge and the needle could be withdrawn back into a cell or container within the insertion mechanism. This embodiment may be advantageous because it protects the needle and may eliminate the need for a separate or individual sharps container when the magazine is disposed of.

In another embodiment, the sterile capsule is a hollow cavity. The insertion mechanism comprises a piston. The insertion mechanism is operable for pushing the piston into the hollow cavity for inserting the insertion needle into the subject. The insertion mechanism is further operable for retracting the insertion needle back into the hollow cavity after insertion of the sensor into the subject using the piston. This embodiment may be advantageous because the hollow cavity performs multiple functions. First it provides the sterile capsule to keep the insertion needle and sensor sterile and then later it also serves as a means of protecting the needle after use.

In another embodiment, the sterile capsule comprises a seal for sealing the sterile capsule. The use of a seal is advantageous because it keeps the contents of the sterile capsule from becoming contaminated.

In another embodiment, the seal is a septum. The insertion mechanism is operable for pushing the insertion needle through the septum. The septum is operable for attaching to a sensor mounting unit with an adhesive for attaching to the outer surface of the subject. The sensor mounting unit is able to be attached to the subject using the adhesive. For instance the adhesive may be a surface that holds the mounting unit onto the subject. In this embodiment the insertion needle is pressed through the septum and the mechanism also pushes the septum such that it attaches or sticks to the sensor mounting unit. After insertion the septum is operable for remaining fixed to the mounting unit and the insertion needle is withdrawn. The insertion needle is withdrawn back into the hollow cavity and is therefore protected. In some examples the sensor mounting unit may be a component of the sensor insertion assembly. In other examples the sensor mounting unit may be a separate component that is first attached to the subject using the adhesive and then the sensor insertion assembly inserts the sensor into the subject and the attaches the septum to the sensor mounting unit.

In another embodiment, the seal is a pre-stressed foil. The insertion mechanism is operable for pushing the insertion needle through the pre-stressed foil. The pre-stressed foil is operable for opening the sterile capsule when pierced by the insertion needle. When the needle pierces the pre-stressed foil the stresses within the pre-stressed foil cause the pre-stressed foil to open automatically. Essentially the needle weakens the pre-stressed foil and the forces already present in the pre-stressed foil cause it to open.

In another embodiment, the insertion mechanism is operable for actuating a cable when actuating the insertion needle. The cable is operable for removing the seal when actuated. This may be implemented in a variety of ways. For instance if the sterile capsule is a hollow cavity and the insertion mechanism is used when the piston is actuated it may also pull on a cable which is used to remove the seal.

In another embodiment, the sterile capsule contains a coil. The coil is operable for cutting open the seal when the insertion needle is actuated. For instance in the use of a hollow cavity there may be a cylindrical coil or spring within the cavity. A knife-edge or sharp cutting edge may be at the end of the spring in contact with the seal. As a piston is actuated the coil spins and cuts open the seal.

In another embodiment, the chamber comprises a chamber knife-edge mount for receiving the sterile capsule. The chamber knife-edge mount as used herein is a knife-edge mounting or mount located in the chamber. The knife-edge mount is operable for opening the seal when the insertion mechanism is actuated. For instance the actuation of the insertion mechanism could cause the sterile capsule to be pressed against the knife-edge in such a way that the seal opens.

In another embodiment, the sterile capsule is in a fixed position and the knife-edge mount is moved during the actuation of the insertion mechanism such that the seal is opened.

In another embodiment, one of the sterile capsule and the inserter comprises a spring mechanism. The spring mechanism is operable for being put under stress when the sterile capsule is inserted into the chamber. The spring mechanism is operable for opening the seal when the insertion mechanism is actuated. This embodiment may be beneficial because the work necessary for opening the seal is stored in the spring mechanism. This reduces the amount of force necessary to actuate the insertion mechanism. This may make it easier or more pleasant for a subject to use the sensor insertion assembly for inserting the sensor.

In another embodiment, the insertion mechanism is operable for removing the seal automatically during actuation of the insertion needle. This embodiment may be advantageous because the operator of the insertion assembly does not need to worry about removing the seal. Depending upon the features of the insertion mechanism, the opening of the sterile capsule and/or the insertion of the insertion needle and/or the retraction of the insertion needle and/or the mounting of the sensor or a portion of the sensor onto a mounting base may be performed automatically by the insertion mechanism.

In another embodiment, the sensor cartridge further comprises a sensor connector connected to the sensor. The insertion mechanism is operable for mounting the sensor connector into a sensor mounting unit upon actuation of the insertion needle.

In some examples, the sensor mounting unit may be a component of the sensor insertion assembly. The sensor cartridge may comprise the sensor mounting unit.

In other examples, the sensor mounting unit may be a separate component that is first operable to be attached to the subject using the adhesive and then the sensor insertion assembly is operable to insert the sensor into the subject and attach the sensor connector to the sensor mounting unit.

In another embodiment, the sensor mounting unit comprises a knife edge mount for receiving the sterile capsule. The knife edge mount is operable for opening the seal. The insertion mechanism may press the seal against the knife edge mount when the insertion mechanism is actuated and open the seal. Alternatively, a user may press the sterile capsule against the knife edge mount during the process of aligning the sensor insertion assembly to the sensor mounting unit.

In another embodiment, the sensor connector is not mounted into a sensor mounting unit. The sensor may be left free or hanging.

In another embodiment, the sensor connector is inserted automatically into an electronic component instead of into the sensor mounting unit. The electronic component may, for example, be for logging or transmitting sensor data.

In another embodiment, the sensor is an electrochemical sensor.

In another embodiment, the sensor is any one of the following: a glucose sensor, a lactate sensor, and an oxygen sensor.

In another aspect, this disclosure provides for a sensor cartridge as described in any one of the preceding embodiments.

In another aspect, this disclosure provides for an inserter as described in any one of the preceding embodiments.

In another aspect, this disclosure provides for a sensor cartridge comprising an insertion needle and a sensor within a sterile capsule. The sensor cartridge is operable for insertion into a chamber of an inserter. The insertion needle is operable for being actuated by an insertion mechanism of the inserter. The sensor cartridge is operable for removal from the chamber. The sensor cartridge is operable for shielding the insertion needle upon removal of the sensor cartridge from the chamber. The advantages of this have been previously discussed.

In another aspect, this disclosure provides for an inserter comprising a chamber for receiving a sensor cartridge according to an embodiment of this disclosure.

It is understood that one or more of the aforementioned embodiments may be combined as long as the combined embodiments are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Like numbered elements in these figures are either equivalent elements or perform the same function. Elements which have been discussed previously will not necessarily be discussed in later figures if the function is equivalent.

Figure 1:
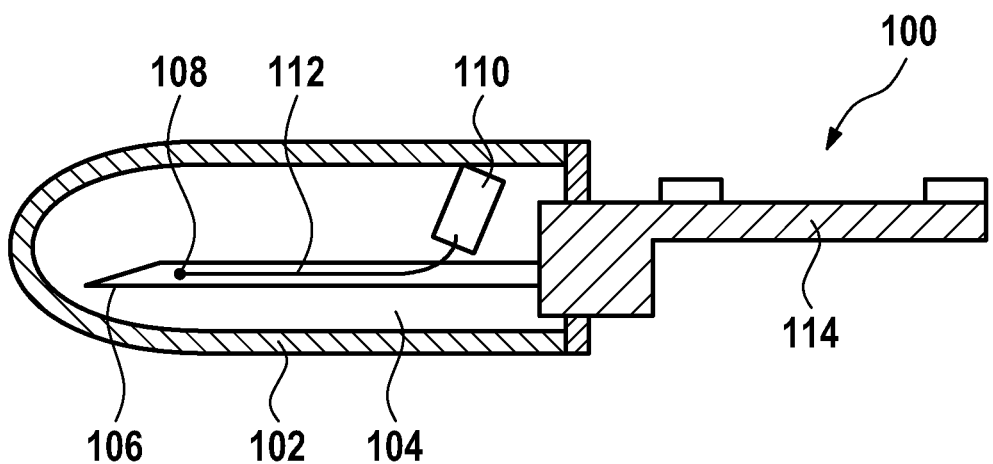
FIG. 1 illustrates a sensor cartridge according to this disclosure.

FIG. 1 illustrates a sensor cartridge 100 according to an embodiment. The sensor cartridge 100 comprises a cap 102 which encloses a sterile capsule 104. Within the sterile capsule 104 there is an insertion needle 106 and a sensor 108. The insertion needle 106 has a hollow channel, is flat or has a rolled structure which enables the sensor to be inserted subcutaneously into a subject. There is further within the sterile capsule 104 a sensor connector 110 which is connected to the sensor 108 via an electrical connection 112. The needle 106 is connected to a mechanical connector 114. The mechanical connector 114 is adapted to being connected to an insertion mechanism operable for actuating the insertion needle 106. In some embodiments the mechanical adaptor 114 is adapted for locking or snapping into the insertion mechanism. In other embodiments the mechanical adaptor 114 is a sliding carriage.

Figure 2:
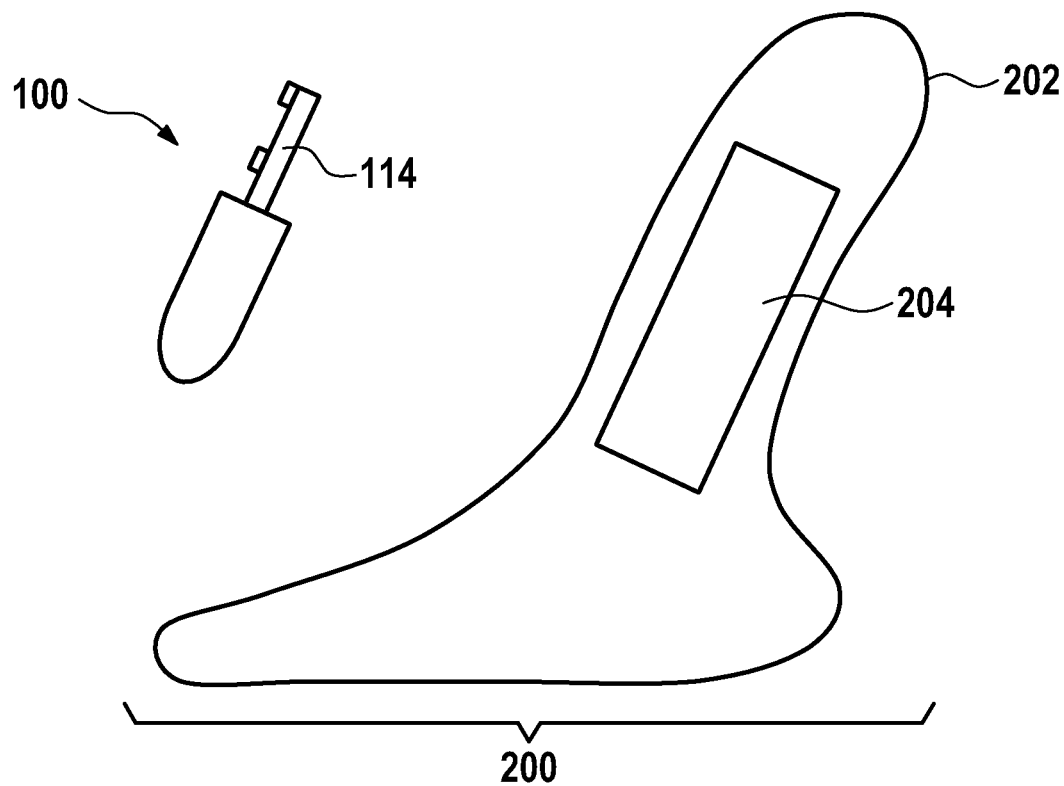
FIG. 2 illustrates a sensor insertion assembly according to this disclosure.

FIG. 2 shows a sensor insertion assembly 200 according to an embodiment of this disclosure. The sensor insertion assembly 200 comprises a sensor cartridge 100 according to an embodiment of this disclosure. The sensor insertion assembly 200 further comprises an inserter 202 with a chamber 204 operable for receiving the sensor cartridge 100. The sensor cartridge 100 can be placed into the chamber 204. An actuator of some form which is not shown in this Fig. is then used to drive the insertion needle 106 to insert the sensor 108 into the subject. The sensor cartridge 100 is able to be removed from the chamber 204 after the insertion needle has been actuated. The inserter 202 is reusable as a new sensor cartridge 100 can be installed in the chamber 204.

Figure 3:
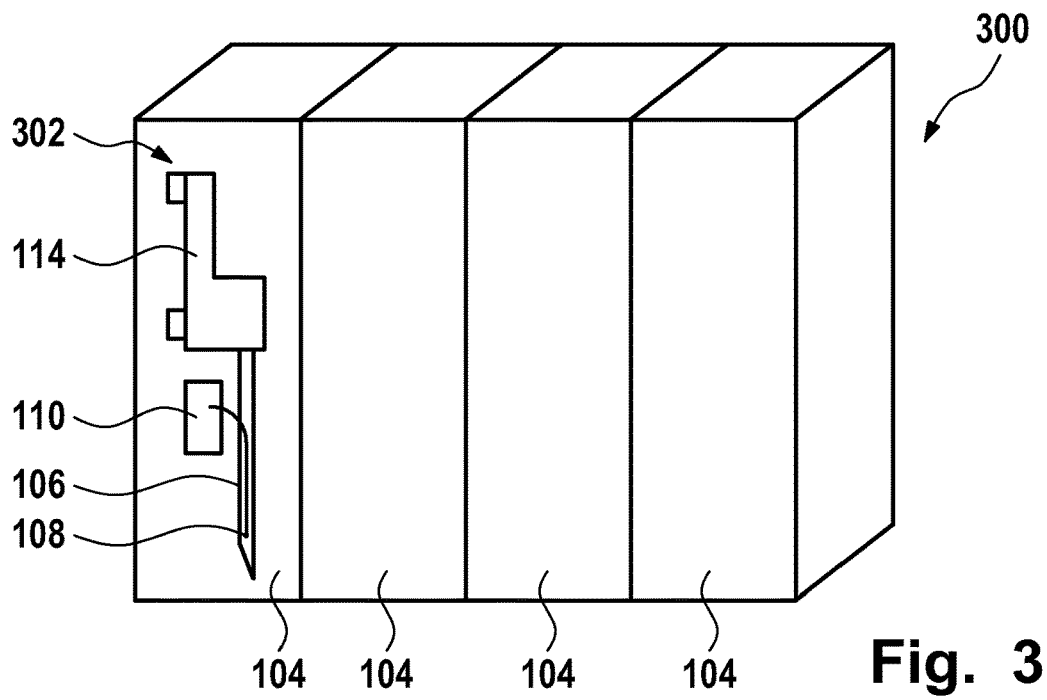
FIG. 3 illustrates a magazine according to this disclosure.

FIG. 3 shows a magazine 300 according to an embodiment of this disclosure. The magazine 300 shows a linear arrangement of four sterile capsules 104. Within each of the sterile capsules is a needle 106, with a sensor 108 in an arrangement similar to that shown in FIG. 1. In this embodiment the magazine 300 forms the sterile capsules 104. Within one of the sterile capsules 104 a sensor cartridge 302 is shown. In an alternative embodiment the sensor cartridge 100 of FIG. 1 could also be placed within a magazine.

Figure 4:
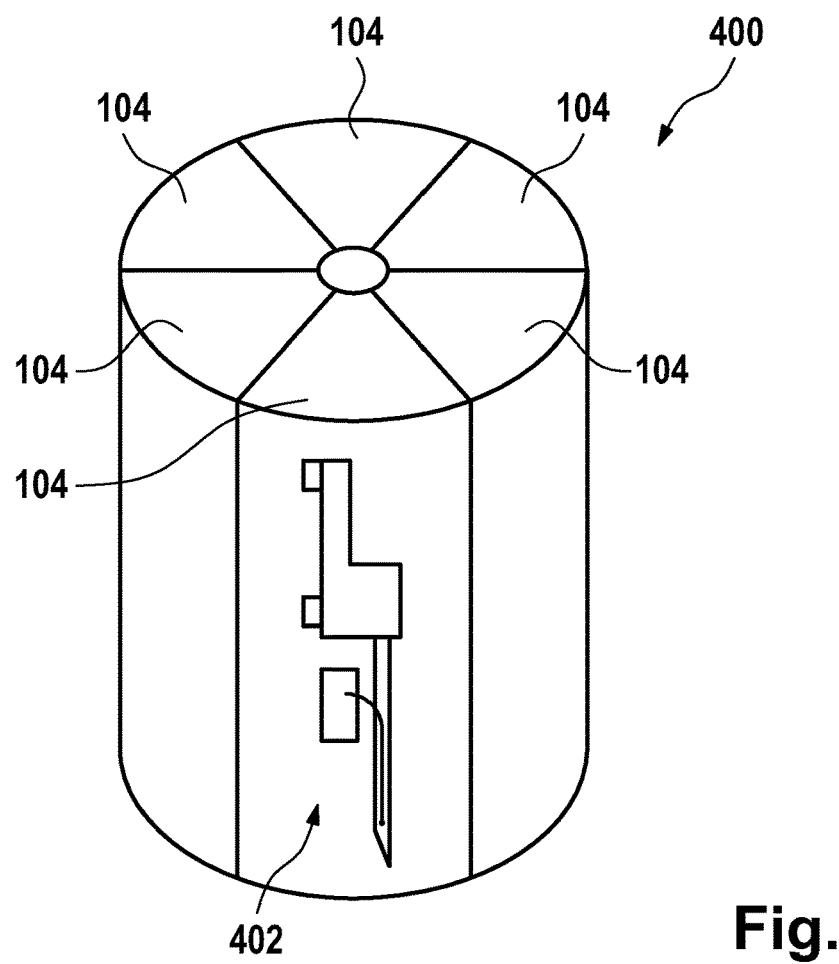
FIG. 4 illustrates a magazine 400 according to a further embodiment.

FIG. 4 shows an alternative embodiment of the magazine 400 according to this disclosure. In this embodiment a series of sterile capsules 104 are arranged in a cylindrical configuration. In this example the inserter would change to different sensor cartridges 402 by rotating the magazine 400 in the same way that a revolver would change cartridges. A sensor cartridge 402 similar to that shown in FIG. 3 is shown in one of the sterile capsules 104. In an alternative embodiment a sensor cartridge 100 according to FIG. 1 is used instead.

In the various embodiments the sterile capsule and the sterile magazine may be used as a container for storing the used insertion needles. In the embodiments with the magazine the needle may not be reachable by a finger.

Figure 5:
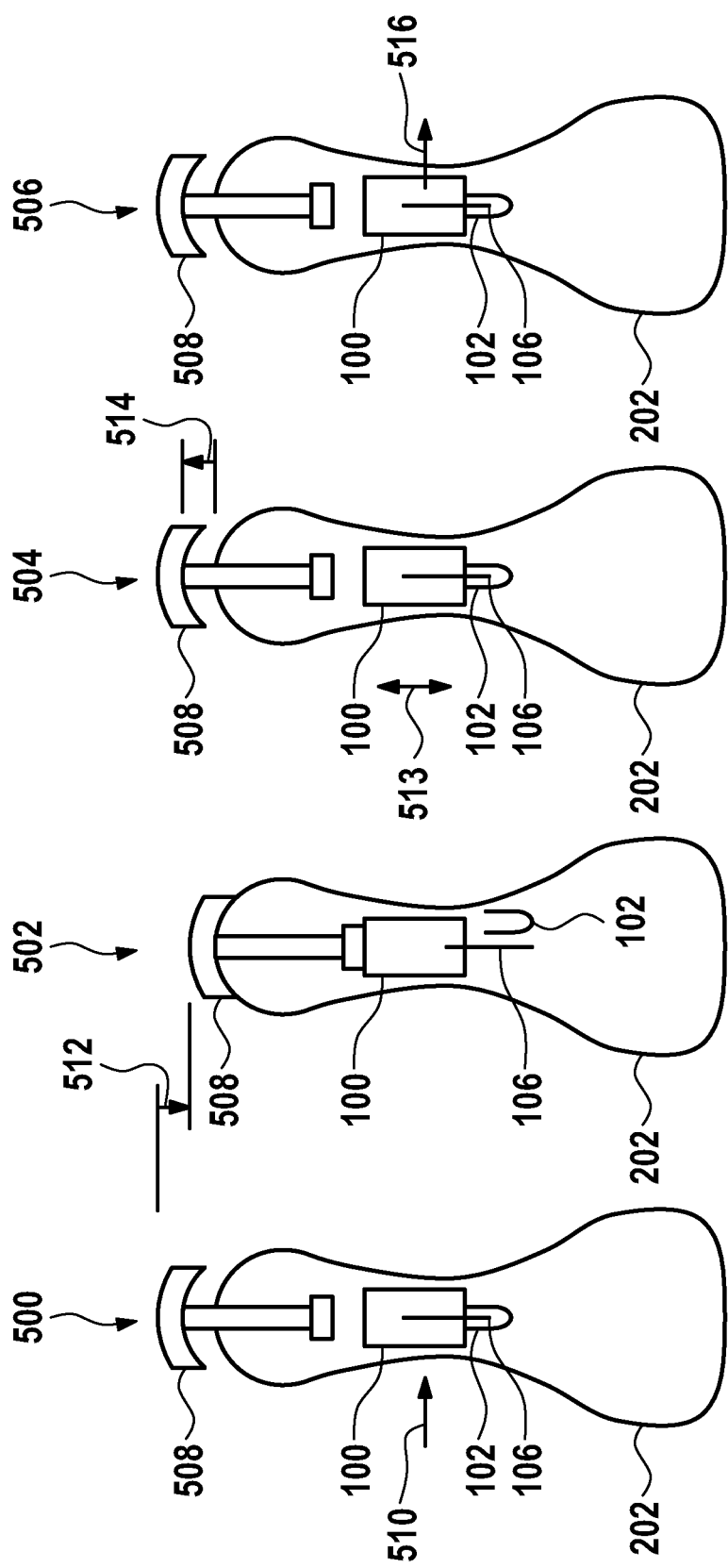
FIG. 5 illustrates an example of a failsafe mechanism according to an embodiment.

FIG. 5 shows an example of a failsafe mechanism 508 according to an embodiment of this disclosure. In this example an inserter 202 with a sensor cartridge 100 is shown. There are four views, a first view 500, a second view 502, a third view 504 and a fourth view 506. In the first view 500 the cartridge 100 is inserted 510 into the chamber. Next in view 2, a plunger 508 is depressed as shown by arrow 512. This loads the sensor cartridge 100 and the cap 102 which was protecting the insertion needle 106 is removed. Next, as shown in view 504, the sensor may be inserted by actuating the needle as indicated by arrow 513. After use of the inserter 202 the plunger 508 is then retracted as indicated by arrow 514. This moves the cap 102 back into a protective place for protecting the insertion needle 106. Finally in view 506 the sensor cartridge 100 is removed from the chamber as indicated by arrow 516.

Figure 6:
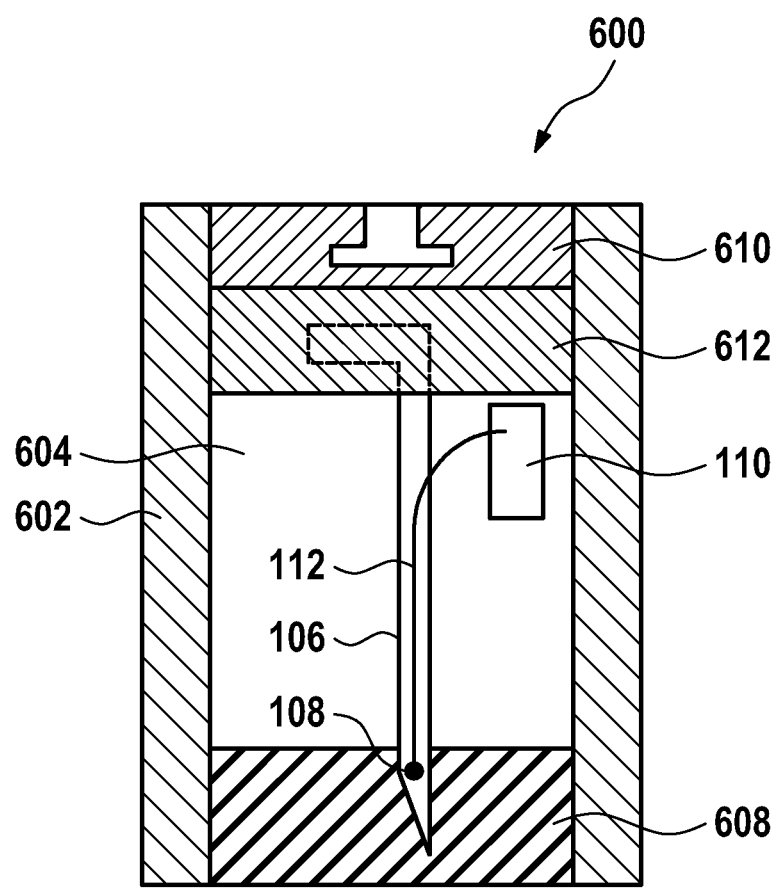
FIG. 6 illustrates a sensor cartridge according to a further embodiment.

FIG. 6 shows a sensor cartridge 600 according to an embodiment of this disclosure. The sensor cartridge 600 is formed by a tube 602 which forms a sterile capsule or hollow cavity 604. On one end a septum 608 seals the tube 602. On the other end a mechanical actuator or adapter 610 is in contact with a top seal 612. The mechanical adapter 610 can be used to drive an insertion needle 106 through the septum 608 and also retract it. There is also a sensor 108 within the sterile capsule 604.

Figure 7:
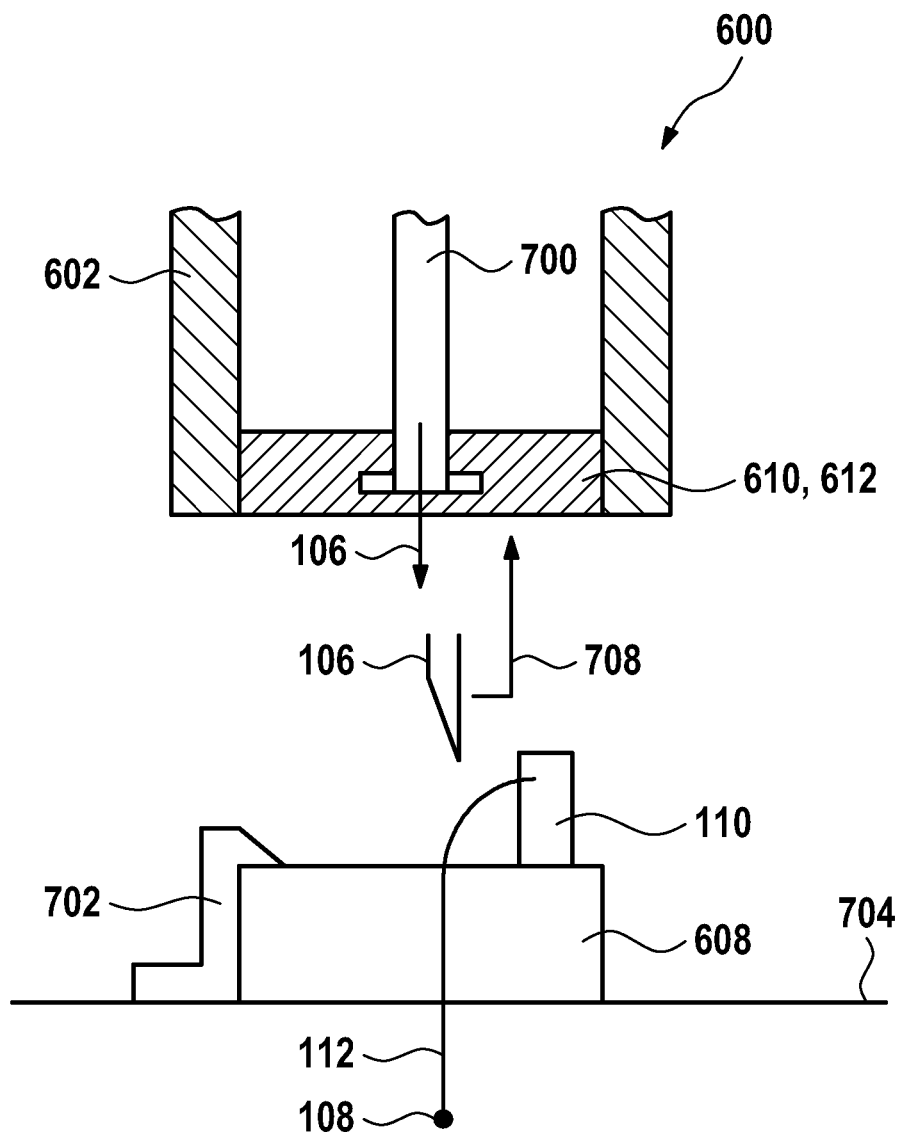
FIG. 7 illustrates the operation of the sensor cartridge shown in FIG. 6.

FIG. 7 illustrates the operation of the sensor cartridge 600 as shown in FIG. 6. A portion of an insertion mechanism 700 is shown as being attached to the mechanical adapter 610. The mechanical adapter has been used to drive the insertion needle 106 through the surface 704 of a subject. A sensor mounting unit 702 is attached to the surface of the subject 704. A sensor 108 has been inserted into the subject and the electrical connection 112 goes back to the sensor connector 110. The septum 608 is left in place and is connected to the sensor mounting unit 702. The insertion needle 106 is withdrawn 708. The retraction of the insertion mechanism 700 causes the insertion needle 106 to be withdrawn back into the tube 602.

Figure 8:
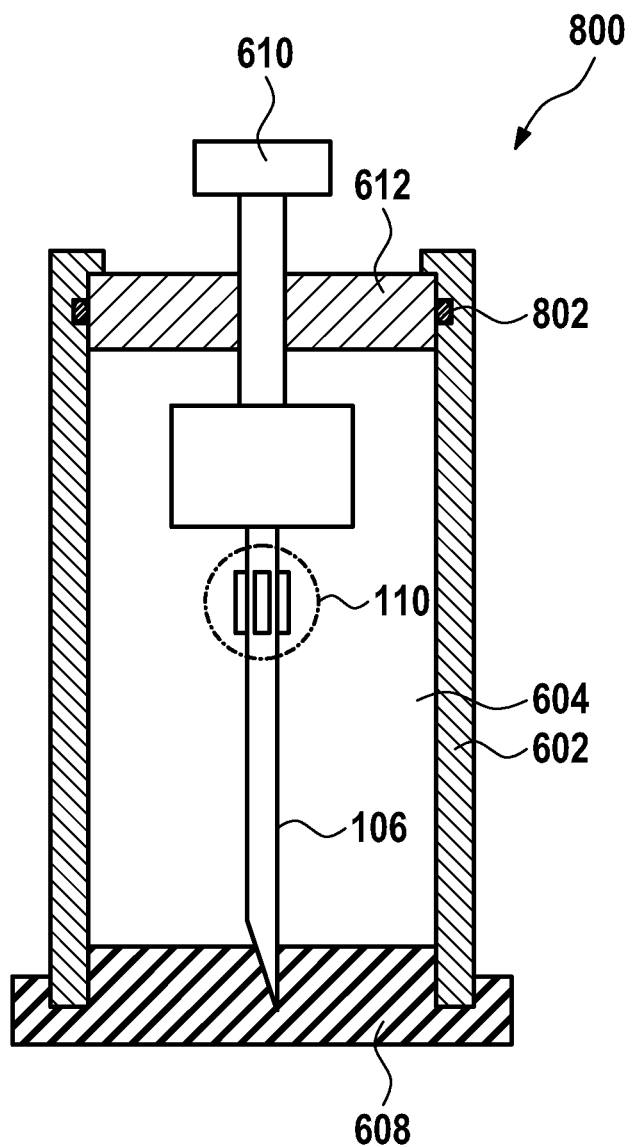
FIG. 8 illustrates a sensor cartridge according to a further embodiment.

FIG. 8 shows an alternative embodiment of a sensor cartridge 800. In this embodiment there is also a tube 602 sealed at one end by a septum 608. A mechanical adapter or piston 610 is used to push the insertion needle 106 through the septum 608. There is again a top seal 612 which is additionally sealed by O-rings 802.

Figure 9:
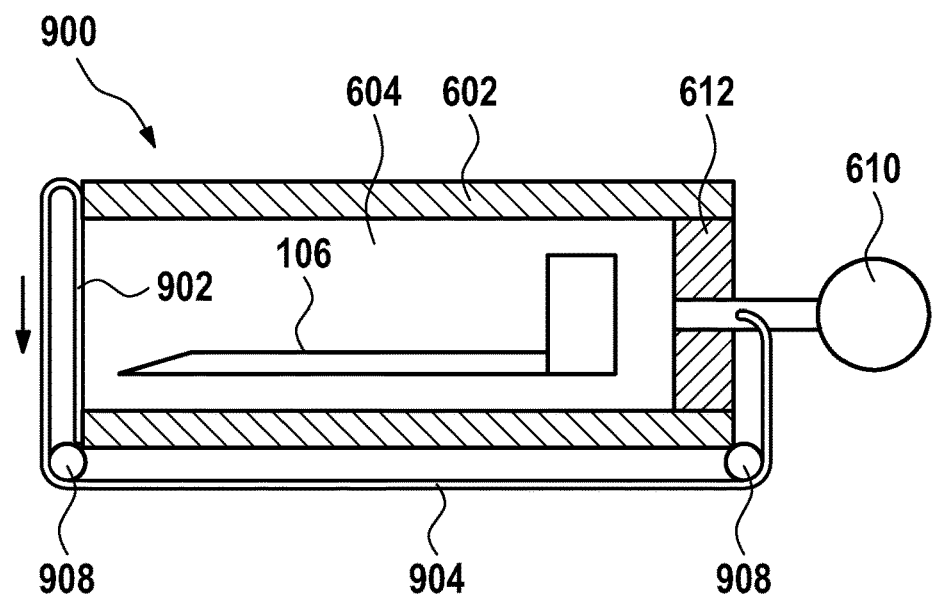
FIG. 9 illustrates a sensor cartridge according to a further embodiment.

FIG. 9 shows a further example of a sensor cartridge 900 according to an embodiment of this disclosure. Again the sensor cartridge is in a tube-like configuration with a mechanical adapter 610 that acts as a piston. In this embodiment there is a seal 902 sealing one end. There is a cable 904 attached to one end of the seal 902. The cable is guided along rollers 908 and is connected to the mechanical adapter 610. When the mechanical adapter 610 is actuated it pulls on the cable 904 which then in turn pulls open the seal 902.

Figure 10:
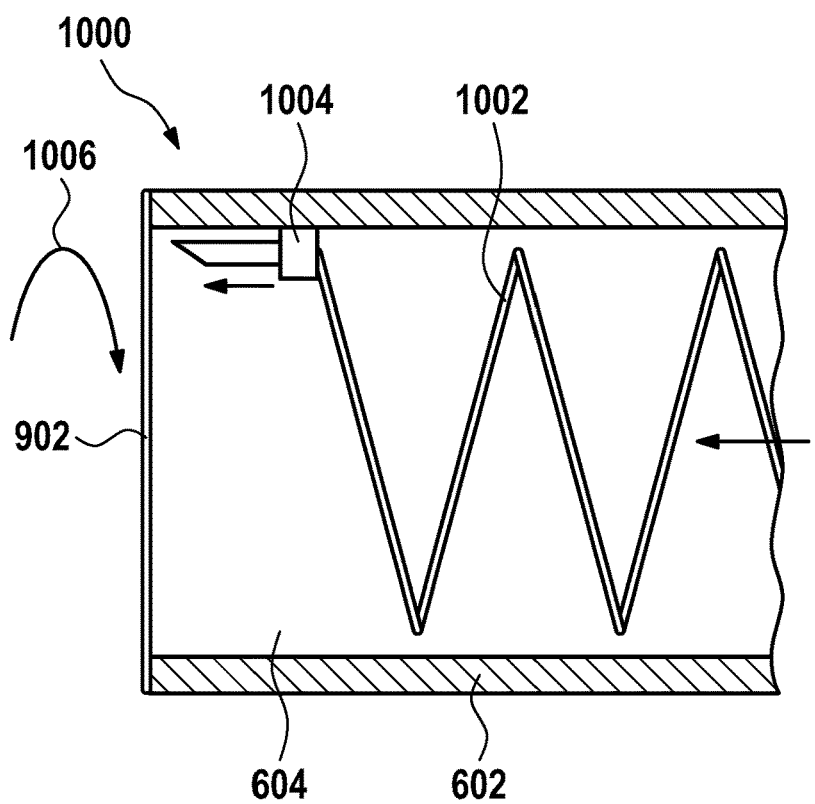
FIG. 10 illustrates a portion of a sensor cartridge according to a further embodiment.

FIG. 10 shows a portion of a sensor cartridge 1000 according to a further embodiment of this disclosure. The embodiment shown in FIG. 10 is similar to that shown in FIG. 9 except a different mechanism is used for opening the seal 902. In this case a spring or coil 1002 is within the tube 602. As a mechanical actuator is depressed it compresses the coil 1002 which causes a cutting edge 1004 in contact with the seal 902 to spin 1006. This causes the seal 902 to open.

Figure 11:
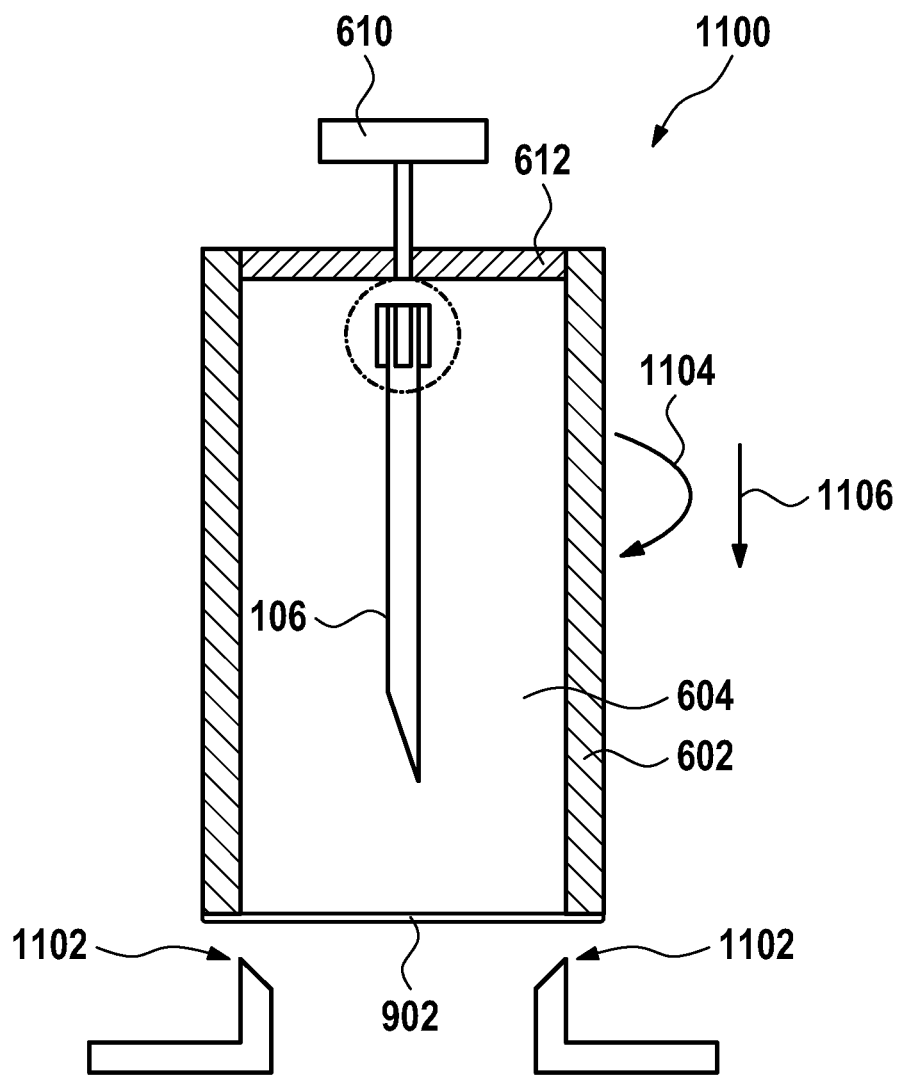
FIG. 11 illustrates a sensor cartridge according to a further embodiment.

FIG. 11 shows a further example of an embodiment of a sensor cartridge 1100 according to this disclosure. The sensor cartridge 1100 is again a tubular or cylindrical type sensor cartridge. There is a seal 902 which seals the sterile capsule or hollow cavity 604. The sensor cartridge 1100 when inserted into the inserter undergoes a movement to open the seal 902. The sensor cartridge 1100 may either be rotated or directly put 1104 or direct pushed to cause a motion in the direction 1106. The motion in direction 1106 causes the sensor cartridge 1100 to force the seal 1102 against a knife-edge 1102 of the inserter. This causes the seal 902 to open.

In an alternative interpretation of FIG. 11, the knife edge mount (1102) is on a sensor mounting unit. The insertion mechanism may actuate the sensor cartridge or the knife edge mount to open the seal. Alternatively, the operator may bring the sensor cartridge into contact with the knife edge before actuating the insertion mechanism. The knife edge may also serve as a means of aligning the sensor insertion assembly to a sensor mounting unit.

Figure 12:
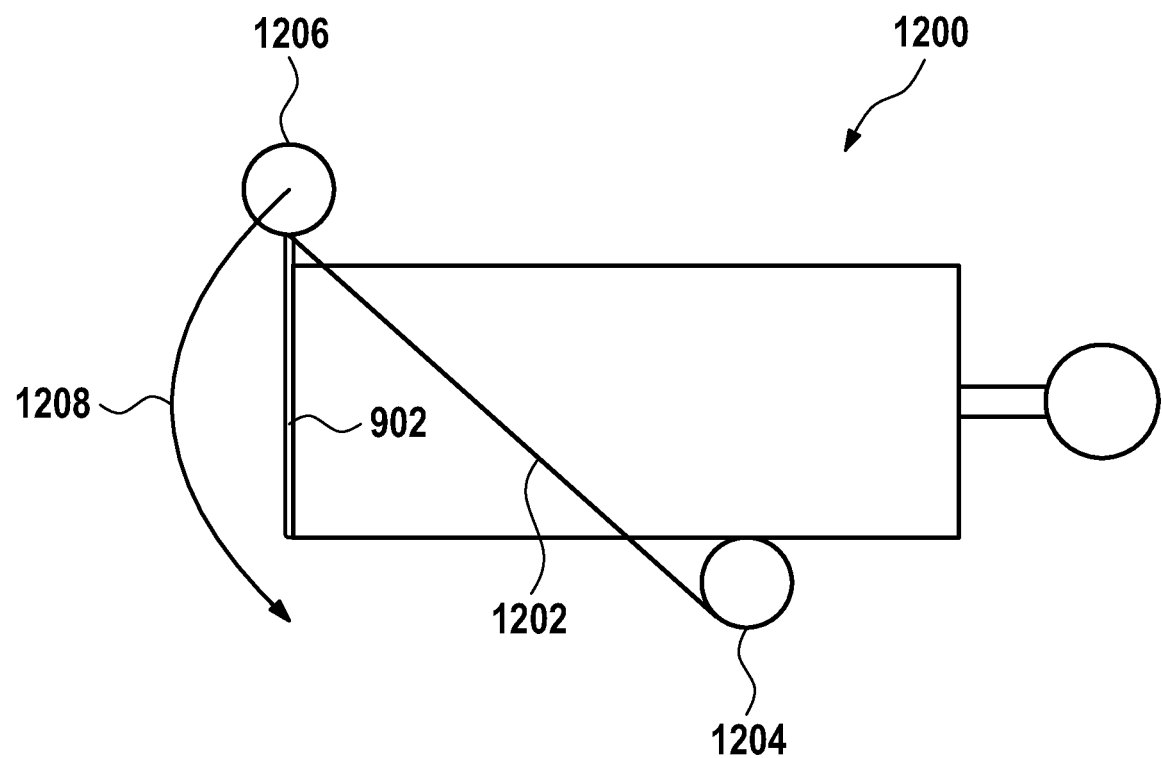
FIG. 12 illustrates a sensor cartridge according to a further embodiment.

FIG. 12 shows a further embodiment of a sensor cartridge 1200 according to this disclosure. In this embodiment the sensor cartridge 1200 is a cylindrical type sensor cartridge. There is a spring 1202 which is anchored at one point 1204. When the sensor cartridge 1200 is loaded into the chamber it causes the spring 1202 to have one end moved to a loaded position 1206. When the sensor mechanism is actuated the end of the spring 1206 travels along a trajectory 1208. In the process this rips off the seal 902 of the sensor cartridge 1200.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

| LIST OF REFERENCE NUMERALS | |
|---|---|
| 100 | sensor cartridge |
| 102 | cap |
| 104 | sterile capsule |
| 106 | insertion needle |
| 108 | sensor |
| 110 | sensor connector |
| 112 | electrical connection |
| 114 | mechanical connector |
| 200 | sensor insertion assembly |
| 202 | inserter |
| 204 | chamber |
| 300 | magazine |
| 302 | sensor cartridge |
| 400 | magazine |
| 402 | sensor cartridge |
| 500 | first view |
| 502 | second view |
| 504 | third view |
| 506 | fourth view |
| 508 | plunger |
| 510 | cartridge inserted |
| 512 | plunger depressed |
| 514 | plunger retracted |
| 515 | needle inserted |
| 516 | cartridge removed |
| 600 | sensor cartridge |
| 602 | tube |
| 604 | sterile capsule or hollow cavity |
| 608 | septum |
| 610 | mechanical adaptor or piston |
| 612 | top seal |
| 700 | insertion mechanism (actuator) |
| 702 | sensor mounting unit |
| 704 | surface of subject |
| 708 | retraction of insertion needle |
| 800 | sensor cartridge |
| 802 | O-ring |
| 900 | sensor cartridge |
| 902 | seal |
| 904 | cable |
| 908 | roller |
| 1000 | sensor cartridge |
| 1002 | spring |
| 1004 | cutting edge |
| 1006 | rotation of cutting edge |
| 1100 | sensor cartridge |
| 1102 | knife edge |
| 1104 | rotation |
| 1106 | direction of motion |
| 1200 | sensor cartridge |
| 1202 | spring mechanism |
| 1204 | anchor point |
| 1206 | loaded position |
| 1208 | direction of travel |

The invention claimed is:

1. A sensor insertion assembly, comprising: a sensor cartridge comprising an insertion needle configured for piercing the skin to create a puncture wound through which a sensor is inserted into the skin, the insertion needle and tip thereof disposed within a sealed sterile capsule; the sensor being within the sealed sterile capsule, wherein the sensor is within the insertion needle; and an inserter comprising a chamber for removably receiving the sensor cartridge, the inserter further comprising an actuator operable for actuating the insertion needle for inserting the sensor into a subject; wherein the sensor cartridge is operable for shielding the insertion needle upon removal of the sensor cartridge from the chamber and after inserting the sensor into the subject.

2. The sensor insertion assembly of claim 1, wherein the actuator is operable for removing at least a portion of the insertion needle from the sterile capsule a predetermined time before inserting the sensor into the subject.

3. The sensor insertion assembly of claim 1, further comprising a magazine having several of the sensor cartridges, wherein the inserter is operable for reloading a second sensor cartridge into the chamber from the magazine after actuation of the actuator, and wherein the magazine is any one of: a linear magazine and a cylindrical magazine.

4. The sensor insertion assembly of claim 3, wherein the magazine is operable for shielding of the insertion needle after actuation of the actuator.

5. The sensor insertion assembly of claim 1, wherein the sterile capsule comprises a hollow cavity, wherein the actuator comprises a piston and is operable for pushing the piston into the hollow cavity for inserting the insertion needle into the subject, wherein the actuator is further operable for retracting the insertion needle back into the hollow cavity after insertion of the sensor into the subject using the piston.

6. The sensor insertion assembly of claim 1, wherein the sealed sterile capsule comprises a seal.

7. The sensor insertion assembly of claim 6, wherein:
the seal is a septum;
the actuator is operable for pushing the insertion needle through the septum; and
the septum is operable for attaching to a sensor mounting unit.

8. The sensor insertion assembly of claim 6, wherein the seal is a pre-stressed foil, the actuator is operable for pushing the insertion needle through the pre-stressed foil, and the pre-stressed foil is operable for opening the sterile capsule when pierced by the insertion needle.

9. The sensor insertion assembly of claim 6, wherein the actuator is operable for actuating a cable when actuating the insertion needle, and wherein the cable is operable for removing the seal when actuated.

10. The sensor insertion assembly of claim 6, wherein the sterile capsule contains a coil, and wherein the coil is operable for cutting open the seal when the insertion needle is actuated.

11. The sensor insertion assembly of claim 6, wherein the chamber comprises a knife edge mount for receiving the sterile capsule, and wherein the knife edge mount is operable for opening the seal when the actuator is actuated.

12. The sensor insertion assembly of claim 6, wherein one of the sterile capsule and the inserter comprises a spring mechanism, wherein the spring mechanism is operable for being put under stress when the sterile capsule is inserted into the chamber, wherein the spring mechanism is operable for opening the seal when the actuator is actuated.

13. The sensor assembly of claim 6, wherein the actuator is operable for removing the seal automatically during actuation of the insertion needle.

14. The sensor assembly of claim 6, wherein the sensor cartridge further comprises a sensor connector connected to the sensor, wherein the actuator is operable for mounting the sensor connector into a sensor mounting unit upon actuation of the insertion needle, wherein sensor mounting unit comprises a knife edge mount for receiving the sterile capsule, and wherein the knife edge mount is operable for opening the seal.

15. The sensor assembly of claim 1, wherein the sensor cartridge further comprises a sensor connector connected to the sensor, and wherein the actuator is operable for mounting the sensor connector into a sensor mounting unit upon actuation of the insertion needle.

16. A sensor cartridge, comprising: an insertion needle configured for piercing the skin to create a puncture wound through which a sensor is inserted into the skin, the insertion needle and Up thereof disposed within a sealed sterile capsule; the sensor being within the sterile capsule, wherein the sensor is within the insertion needle; wherein the sensor cartridge is removably receivable in a chamber of an inserter; and wherein the sterile capsule is configured to shield the insertion needle upon removal of the sensor cartridge from the chamber and after inserting the sensor into a subject.

17. A sensor insertion assembly, comprising:
a sensor cartridge comprising an insertion needle and tip thereof disposed within a sterile capsule and a sensor within the sterile capsule, wherein the sensor is within the insertion needle; and
an inserter comprising a chamber for removably receiving the sensor cartridge, the inserter further comprising an actuator operable for actuating the insertion needle for inserting the sensor into a subject, wherein the inserter is configured for use with a magazine having several of the sensor cartridges, wherein the inserter is operable for reloading a second sensor cartridge into the chamber from the magazine after actuation of the actuator, and wherein the magazine is any one of: a linear magazine and a cylindrical magazine; and
wherein the sensor cartridge is operable for shielding the insertion needle upon removal of the sensor cartridge from the chamber and after inserting the sensor into the subject.

18. The sensor insertion assembly of claim 17, wherein the magazine is operable for the shielding of the insertion needle after actuation of the actuator.

19. The sensor insertion assembly of claim 17, wherein the sterile capsule comprises a seal for sealing the sterile capsule.

20. The sensor insertion assembly of claim 19, wherein:
the seal is a septum;
the actuator is operable for pushing the insertion needle through the septum; and
the septum is operable for attaching to a sensor mounting unit.

21. The sensor assembly of claim 19, wherein the actuator is operable for removing the seal automatically during actuation of the insertion needle.

22. A sensor insertion assembly, comprising:
a sensor cartridge comprising an insertion needle and tip thereof disposed within a sterile capsule and a sensor within the sterile capsule, wherein the sensor is within the insertion needle; and an inserter comprising a chamber for removably receiving the sensor cartridge, the inserter further comprising an actuator operable for actuating the insertion needle for inserting the sensor into a subject;

wherein the sensor cartridge is operable for shielding the insertion needle upon removal of the sensor cartridge from the chamber and after inserting the sensor into the subject; and wherein the sterile capsule comprises a hollow cavity and the actuator comprises a piston operable to enter the hollow cavity.

23. The sensor insertion assembly of claim 22, wherein the actuator is operable for pushing the piston into the hollow cavity for inserting the insertion needle into the subject.

24. The sensor insertion assembly of claim 23, wherein the actuator is further operable for retracting the insertion needle back into the hollow cavity after insertion of the sensor into the subject using the piston.

25. The sensor insertion assembly of claim 22, wherein the sterile capsule comprises a seal for sealing the sterile capsule.

26. The sensor insertion assembly of claim 25, wherein:
the seal is a septum;
the actuator is operable for pushing the insertion needle through the septum; and
the septum is operable for attaching to a sensor mounting unit.

* * * * *

UNITED STATES PATENT AND TRADEMARK OFFICE
CERTIFICATE OF CORRECTION

PATENT NO. : 10,653,445 B2
APPLICATION NO. : 14/553380
DATED : May 19, 2020
INVENTOR(S) : Frey et al.

Page 1 of 1

It is certified that error appears in the above-identified patent and that said Letters Patent is hereby corrected as shown below:

In the Claims

Claim 16, Column 10, Lines 20-21, the phrase "the insertion needle and Up thereof" should read --the insertion needle and tip thereof--.

Signed and Sealed this
Eleventh Day of August, 2020

Andrei Iancu
*Director of the United States Patent and Trademark Office*